US00PP15167P2

(12) United States Plant Patent
Olesen et al.

(10) Patent No.: US PP15,167 P2
(45) Date of Patent: Sep. 21, 2004

(54) ROSE PLANT NAMED 'POULEN011'

(50) Latin Name: *Rosa hybrida*
Varietal Denomination: POULen011

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 11 days.

(21) Appl. No.: 10/738,150

(22) Filed: Dec. 16, 2003

(51) Int. Cl.[7] ..... A01H 5/00
(52) U.S. Cl. ..... Plt./138
(58) Field of Search ..... Plt./138, 137, 148, Plt./149

*Primary Examiner*—Anne Marie Grunberg
*Assistant Examiner*—June Hwu

(57) ABSTRACT

A new garden rose plant of the hybrid tea class which has abundant, pink flowers and attractive foliage. This new and distinct variety has shown to be uniform and stable in the resulting generations from asexual propagation.

2 Drawing Sheets

Botanical classification: *Rosa hybrida.*
Variety denomination: 'POULen011'.

SUMMARY OF THE INVENTION

The present invention constitutes a new and distinct variety of garden rose plant which originated from a controlled crossing between the female parent plant, an unnamed seedling, and the male parent 'POULsyng', described and illustrated in U.S. Plant patent application Ser. No. 09/268,299 dated Mar. 16, 1999, now abandoned. The two parents were crossed during the summer of 1995 and the resulting seeds were planted in a controlled environment in Fredensborg, Denmark. The new variety is named 'POULen011'.

The new variety may be distinguished from its seed parent by the following combination of characteristics:

1. The seed parent has a light pink flower color. 'POULen011' is apricot.
2. The seed parent has a flower diameter, between 80 mm to 100 mm, while the same of 'POULen011' between 100 mm to 150 mm.
3. Whereas the seed parent has a slight fragrance, 'POULen011' has a strong traditional rose fragrance with overtones of lemon.

The new variety may be distinguished from its pollen parent, 'POULsyng', by the following combination of characteristics:

1. The pollen parent has a light pink flower color. 'POULen011' has apricot flowers.
2. The pollen parent has a medium flower size. 'POULen011' has a large flower size.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULen011' from all other varieties of which we are aware.

As part of their rose development program, L. Pernille Olesen and Mogens N. Olesen germinated the seeds from the aforementioned hybridization during winter 1995 and conducted evaluations on the resulting seedlings in a controlled environment in Fredensborg, Denmark.

'POULen011' was selected in the spring 1996 by the inventors as a single plant from the progeny of the aforementioned hybridization.

Asexual reproduction of 'POULen011' by traditional budding and rotted cuttings was first done by L. Pernille and Mogens N. Olesen in their nursery in Fredensborg, Denmark in July, 1996. This initial and other subsequent asexual propagations conducted in controlled environments have demonstrated that the characteristics of 'POULen011' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen011'.

Specifically illustrated in SHEET 1:

FIG. 1.2; Flower bud closed, flower bud as sepals unfold, and partially open;

FIG. 1.3; Flower petals, detached;

Specifically illustrated in SHEET 2:

FIG. 2.2; Bare stem exhibiting thorns;

FIG. 2.3; Mature leaf.

DETAILED DESCRIPTION OF THE VARIETY

Figures 1, 2, 3:
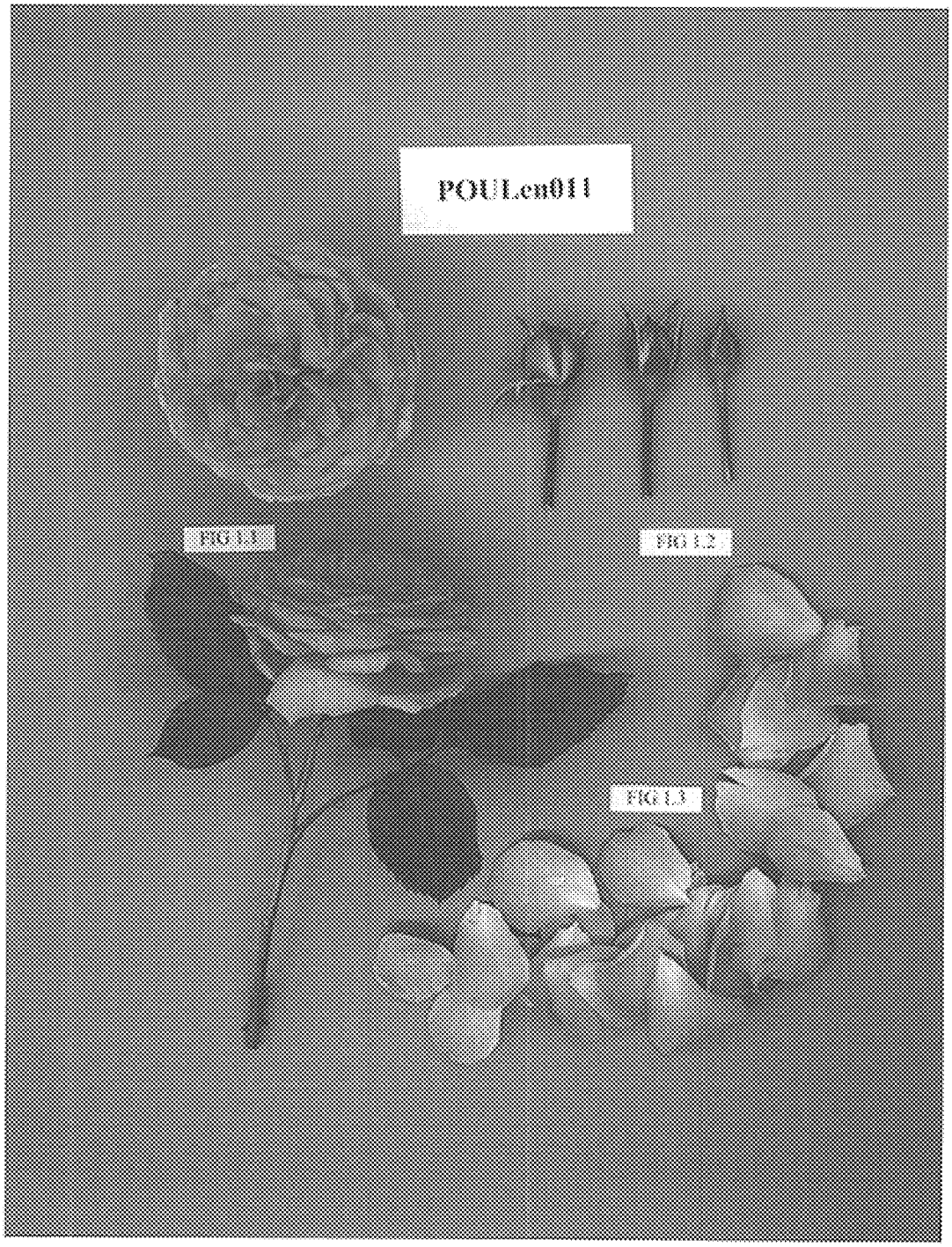
FIG. 1.1; Open flower, stem showing open flower, branching, and the attachment of leaves, buds, and peduncles.
FIG. 2.1; Sepals, receptacle, and peduncle.

The following is a description of 'POULen011', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULdra', a rose variety from the same inventors described and illustrated in U.S. Plant Pat. No. 12,999 dated Sep. 24, 2002, are compared to 'POULen011' in Chart 1.

CHART 1

| | 'POULen011' | 'POULdra' |
|---|---|---|
| General Tonality | Red Group 54D | Red-Purple Group 57B |
| Petalage | 65 | 25–30 |
| Flower Diameter | 80–85 mm. | 100 mm. |

FLOWER AND FLOWER BUD

Blooming habit: Recurrent.

Flower bud:

*Size.*—Upon opening, 25 mm in length from base of receptacle to end of bud.

*Bud form.*—Broad based pointed ovoid.

*Bud color.*—As sepals unfold, petals are Red Group 50A. A distinctive vertical stripe the color of Red Group 46A observed surrounded by Yellow Group 3B blending with Red Group 50A.

*Sepals.*—Upper surface: Color: Yellow-Green Group 145C, at sepal base surrounded by Green Group 139B. Surface: Moderately pubescent. Lower surface: Color: Yellow-Green Group 144A. Anthocyanic intonations of Greyed-Purple Group 183B at sepal apex. Texture: Smooth and glabrous. Shape: Sepal apex is cirrhose. Base is flat at union with receptacle. Margins: No foliaceous appendages observed on three of the five sepals. Margins will produce stipitate glands in sparse quantities. Size: 22 mm (l)×8 mm (w).

*Receptacle.*—Surface: Smooth. Shape: Urn-shaped. Size: 7 mm (h)×10 mm (w). Color: Yellow-Green Group 144A.

*Peduncle.*—Surface: Stipitate glands medium density. Length: 50 to 60 mm. Color: Yellow-Green Group 145B. Anthocyanin: Greyed-Purple Group 184B. Strength: Strong.

*Borne.*—Multiples of 5 buds per flowering stem.

Flower bloom:

*Fragrance.*—Strong traditional rose scent with overtones of lemon.

*Duration.*—The blooms have a duration on the plant of approximately 10 to 12 days. Petals fall cleanly away from plant.

*Size.*—Flower diameter is 80 to 85 mm when open.

*Form.*—Rosette with many overlapping petals.

*Shape of flower when viewed from the side.*—Upon opening, upper part: Flat. Upon opening, lower part: Flattened convex. Open flower, upper part: Flat. Open flower, lower part: Flattened convex.

*Petalage.*—80 petals under normal conditions with 15 petaloids.

Color:

*Upon opening, petals.*—Outermost petals: Outer side: Red Group 54D with weak tones Red Group 54B. Inner side: Red Group 54D. Innermost petals: Outer side: Red Group 54D with tones of Red Group 54B. Inner side: Red Group 54D.

*Upon opening, basal petal spots.*—Outermost petals: Outer side: Yellow Group 10D fading to Yellow-White Group 158D. Inner side: Yellow Group 9C, 3 to 4 mm in length fading sharply to Yellow-White Group 158D. Innermost petals: Outer side: Yellow Group 10D fading to Yellow-White Group 158D. Inner side: Yellow Group 9C, 3 to 4 mm in length fading sharply to Yellow-White Group 158D.

*After opening, petals.*—Outermost petals: Outer side: Red Group 54D with weak tones of Red Group 54B. Inner side: Red Group 54D. Innermost petals: Outer side: Red Group 54D with weak tones of Red Group 54B. Inner side: Red Group 54D.

*After opening, basal petal spots.*—Outermost petals: Outer side: Yellow Group 10D fading to Yellow-White Group 158D. Inner side: Yellow Group 9C, 3 to 4 mm in length fading sharply to Yellow-White Group 158D. Innermost petals: Outer side: Yellow Group 10D fading to Yellow-White Group 158D. Inner side: Yellow Group 9C, 3 to 4 mm in length fading sharply to Yellow-White Group 158D.

General tonality: On open flower Red Group 54D. No change in the general tonality at the end of the 10th day.

*Petals.*—Petal reflex: Slightly. Margin: Entire and uniform. Weak undulations at Apex. Shape: Apex: Round. Base: Acute. Size: 35 to 42 mm (l)×28 to 40 mm (w). Texture: Smooth. Thickness: Average. Arrangement: Not Formal.

*Petaloids.*—Quantity: 12 to 15. Color: Upper surface: Red Group 54D. Lower surface: Red Group 54D with intonations of Red Group 54B. Size: 30 mm (l)×15 mm (w).

Reproductive organs:

*Pistils.*—Length: 6 mm. Quantity: 100.

*Pollen.*—Color: Yellow-Orange Group 21B. Quantity: Scant.

*Anthers.*—Size: 2 mm. Color: Greyed-Orange Group 167A. Quantity: 120 (actual count).

*Filaments.*—Color: Yellow-Orange Group 18B. Length: 7 to 9 mm.

*Stigmas.*—Superior relative to the height and length of the anthers. Color: Yellow-Orange Group 18B with intonations of Red Group 39A.

*Styles.*—Surface: Pubescent. Color: Orange-White Group 159B. Other intonations: Red Group 39D.

*Hips.*—None Observed in the field nursery in Jackson County Oreg.

PLANT

Plant growth: Moderate, upright to bushy. When grown as a budded field grown plant on *Rosa multiflora* understock, the average height of the plant is 114 cm and the average width is 102 cm.

Stems:

*Color.*—Young wood: Yellow-Green Group 144A. Older wood: Yellow-Green Group 144A. Anthocyanin: Greyed-Purple Group 183A.

*Surface texture.*—Young wood: Smooth. Older wood: Smooth.

*Anthocyanin.*—Greyed-Purple Group 183A.

*Thorns.*—Incidence: 15 thorns per 10 cm of stem. Size: 5 mm average. Color: Greyed-Purple Group 183A. Shape: Deeply concave to moderately concave.

Plant foliage: Normal number of leaflets on leaves in middle of the stem: 5 leaflets.

*Compound leaf size.*—150 mm (l)×110 mm (w).

*Color.*—Mature foliage: Upper leaf surface: Green Group 137A. Lower leaf surface: Green Group 138B. Juvenile foliage: Upper leaf surface: Green Group 137A. Lower leaf surface: Green Group 138A.

Plant leaves and leaflets:

*Stipules.*—Size: 25 mm in length. Color: Yellow-green Group 144B. Margins: Medium quantity of stipulate glands observed. Anthocyanin: Color: Greyed-Purple Group 184A.

*Petiole.*—Length: 55 mm. Color: Yellow-Green Group 144B. Margins: Finely serrated with stipitate glands. Anthocyanin: Greyed-Purple Group 184A.

*Rachis.*—Color: Yellow-Green Group 144B. Underneath: Yellow-green Group 144B. Anthocyanin: Color: Greyed-Purple Group 184A.

*Leaflet.*—Size: 50 to 70 mm (l)×30 to 50 mm (w). Edge: Serrated. Shape: Generally ovate. Apex is Cuspidate. Base is Rounded. Texture: Smooth. Arrangement: Odd pinnate. Venation: Reticulate. Glossiness: Moderate Glossy to matte finish.

Disease resistance: Above average resistance to mildew, rust, black spot, and Botrytis under normal growing conditions in Jackson County, Oreg.

Cold hardiness: The variety 'POULen011' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant light pink flowers, strong fragrance, disease resistance, and extended period of bloom.

* * * * *

POULen011

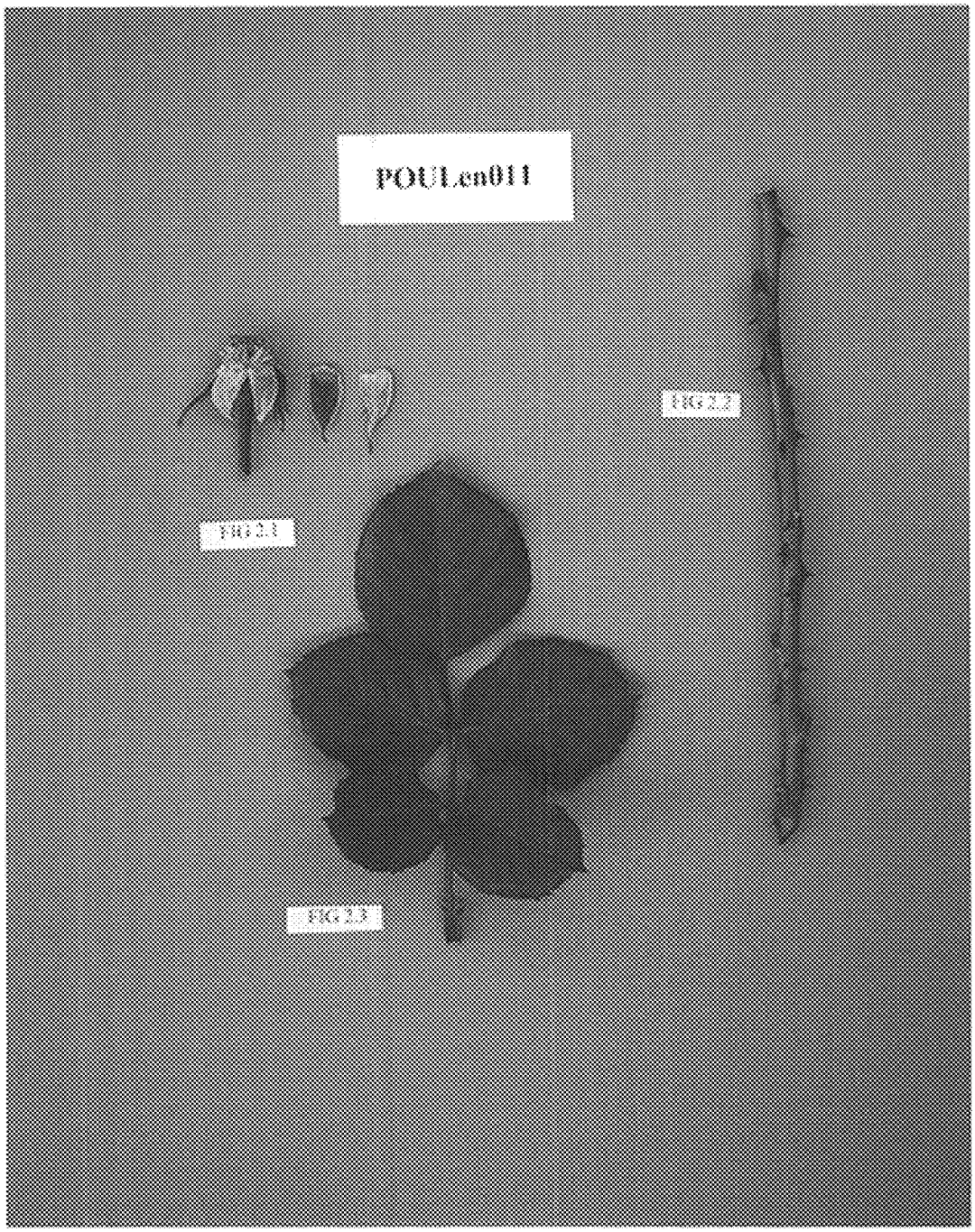
POUL.en011
FIG.2.1
FIG.2.2
FIG.2.3